United States Patent [19]
Sano et al.

[11] Patent Number: 5,588,950
[45] Date of Patent: Dec. 31, 1996

[54] PORTABLE ENDOSCOPE SYSTEM

[75] Inventors: Hiroshi Sano; Hirohisa Ueda; Rensuke Adachi; Kunitoshi Ikeda; Kunikiyo Kaneko; Takashi Koeda, all of Tokyo, Japan

[73] Assignee: Asahi Kogaku Kogyo Kabushiki Kaisha, Tokyo, Japan

[21] Appl. No.: 499,128

[22] Filed: Jul. 7, 1995

[30] Foreign Application Priority Data

| Jul. 11, 1994 | [JP] | Japan | 6-157748 |
| Apr. 20, 1995 | [JP] | Japan | 7-094093 |
| Apr. 20, 1995 | [JP] | Japan | 7-094622 |

[51] Int. Cl.⁶ ............................................. A61B 1/06
[52] U.S. Cl. ................................. 600/178; 600/160
[58] Field of Search ........................... 600/131, 132, 600/178, 179, 160

[56] References Cited

U.S. PATENT DOCUMENTS

| 2,235,979 | 3/1941 | Brown | 600/178 |
| 4,331,403 | 5/1982 | Ohno | 600/132 X |
| 4,580,198 | 4/1986 | Zinnanti, Jr. | 600/178 X |
| 4,941,456 | 7/1990 | Wood et al. | 600/152 |
| 5,077,567 | 12/1991 | Haraguchi et al. | |
| 5,239,983 | 8/1993 | Katsurada. | |
| 5,343,854 | 9/1994 | Katsurada. | |
| 5,377,667 | 1/1995 | Patton et al. | 600/184 |

*Primary Examiner*—Richard J. Apley
*Assistant Examiner*—David R. Risley
*Attorney, Agent, or Firm*—Greenblum & Bernstein P.L.C.

[57] ABSTRACT

A portable endoscope system including an illuminating light guide for transmitting light for illuminating an object, and an illuminating light supply unit for supplying illuminating light to the illuminating light guide. The entrance end portion of the illuminating light guide is disposed in an endoscope control part. The illuminating light supply unit is detachably attached to the control part. The portable endoscope system includes an AC/DC conversion adapter which is connected to an AC power supply to output a predetermined DC voltage and is connectable to the illuminating light supply unit.

9 Claims, 13 Drawing Sheets

PORTABLE ENDOSCOPE SYSTEM

BACKGROUND OF THE INVENTION

The present invention relates to subject matter contained in Japanese Patent Application Nos. 6-157748 (filed on Jul. 11, 1994), 7-94093 (filed on Apr. 20, 1995), and 7-94622 (filed on Apr. 20, 1995), which are expressly incorporated herein by reference in their entireties.

1. Field of the Invention

The present invention relates to a portable endoscope system in which a unit for supplying illuminating light to an illuminating light guide is detachably attached to an endoscope control part.

2. Description of the Prior Art

A conventional portable endoscope system has a light-emitting device for illumination which is provided in an endoscope control part. In such a portable endoscope system, an illuminating light supply unit which contains a miniature bulb and a dry battery as a power supply for the bulb is attached to the control part.

However, when a battery is used as a power supply for the light source, there are cases where the battery runs down, and hence the illumination becomes dark in the middle of an endoscopic inspection (endoscopy), making it impossible to continue the endoscopy.

In such a case, it is extremely troublesome for the doctor to replace the battery during the endoscopy, and it is considerably painful to the patient to be kept waiting during that time. If there is no spare battery, the endoscopy must be stopped. Thus, the prior art presents a serious problem.

SUMMARY OF THE INVENTION

An object of the present invention is to provide a portable endoscope system which needs no replacement of a battery for an illuminating light supply unit, and which has no likelihood that an endoscopy will be interrupted by replacement of a battery as in the case of the prior art.

Other objects and advantages of the present invention will become apparent from the following detailed description of illustrated embodiments of the invention.

According to the present invention, there is provided a portable endoscope system having an illuminating light guide for transmitting light for illuminating an object, and an illuminating light supply unit for supplying illuminating light to the illuminating light guide. The entrance end portion of the illuminating light guide is disposed in an endoscope control part. The illuminating light supply unit is detachably attached to the control part. The portable endoscope system includes an AC/DC conversion adapter which is connected to a commercial AC power supply to output a predetermined DC voltage. The AC/DC conversion adapter is connectable to the illuminating light supply unit.

In addition, there is provided a portable endoscope system having an illuminating light guide for transmitting light for illuminating an object, and an illuminating light supply unit for supplying illuminating light to the illuminating light guide. The entrance end portion of the illuminating light guide is disposed in an endoscope control part. The illuminating light supply unit is detachably attached to the control part. The portable endoscope system includes the following illuminating light supply units which can be selectively used as the above-described illuminating light supply unit, which is detachably attached to the control part: a built-in battery type unit which contains a light source lamp, and a battery for lighting the light source lamp; an AC/DC conversion type unit which has a light source lamp, and an AC/DC converter for obtaining electric power for lighting the light source lamp from a commercial AC power supply; and a light guide cable type unit for transmitting illuminating light from an external light source lamp to the endoscope illuminating light guide through a light guide cable. dr

BRIEF DESCRIPTION OF THE DRAWINGS

The present invention may be more fully understood from the description of preferred embodiments of the invention set forth below, together with the accompanying drawings, in which.

DESCRIPTION OF THE EMBODIMENTS

Embodiments of the present invention will be described below with reference to the accompanying drawings.

Figure 1:
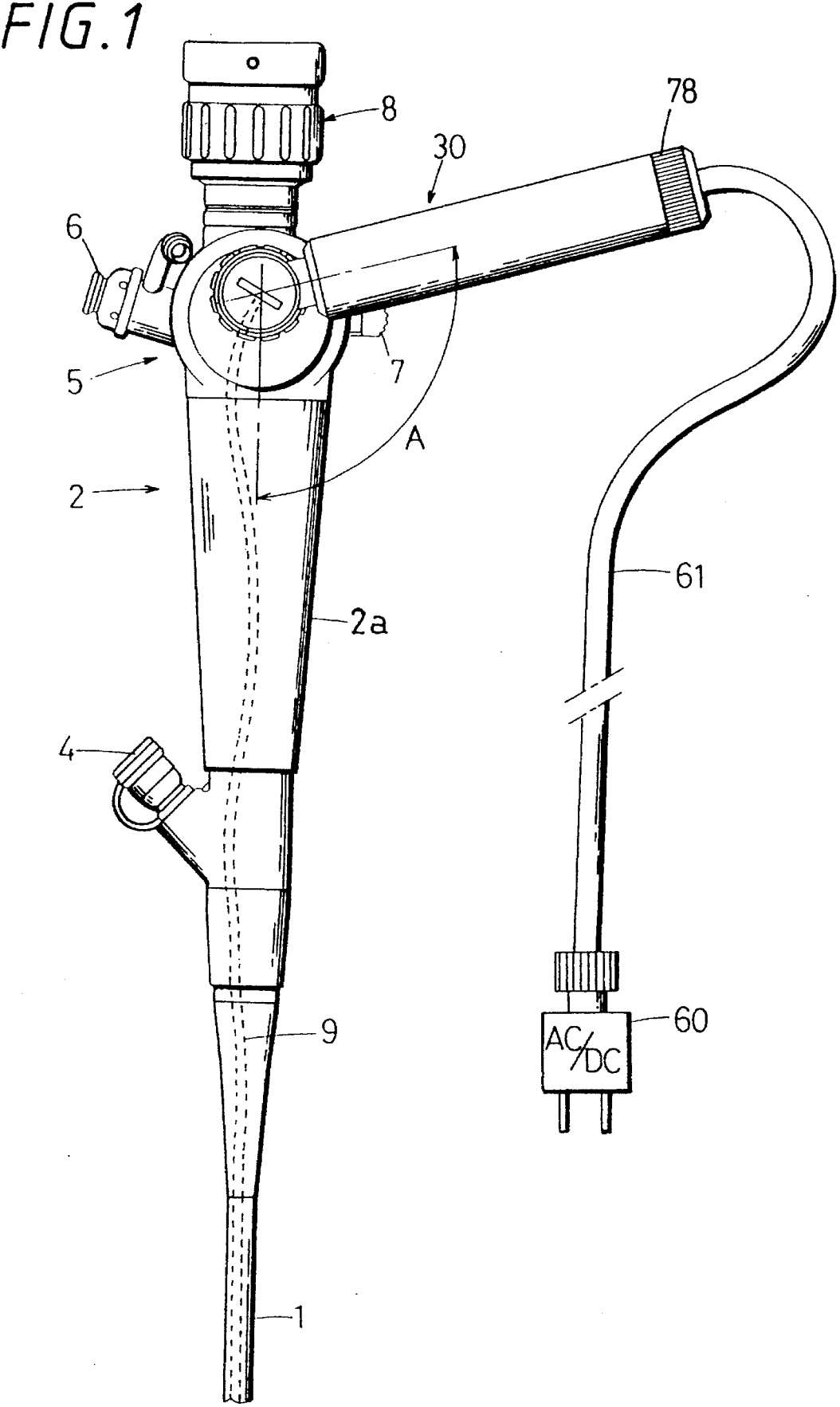
FIG. 1 is a side view showing a first embodiment of the portable endoscope system according to the present invention with an illuminating light supply unit attached to an endoscope control part.

FIG. 1 shows a control part and neighboring constituent elements of a portable endoscope system according to a first embodiment of the present, invention. The portable endoscope system has an insert part 1 which is armored with a flexible tube, and a control part 2 which is connected to the proximal end of the insert part 1.

About three fourths from the bottom of the control part 2 serves as a grip portion 2a. A forceps inlet 4 is provided between the grip portion 2a and the insert part 1 so as to project obliquely forward.

The control part 2 has a control mechanism portion 5 above the grip portion 2a. The control mechanism portion 5 has a suction control valve 6 which is disposed on the front side thereof to carry out a suction operation through a forceps channel (not shown) inserted in the insert part 1. The control mechanism portion 5 further has a bending control lever 7 which is disposed oil the rear side thereof to effect bending control of a remote-controlled bendable portion (not shown) which is formed at the distal end of the insert part 1. In addition, an eyepiece 8 is provided on the top of the control mechanism portion 5.

A light guide fiber bundle 9 for transmitting light for illuminating an object has an entrance end portion thereof disposed in the control mechanism portion 5, and extends through the insert part 1 and the grip portion 2a of the control part 2. The exit end portion of the light guide fiber bundle 9 is disposed In the distal end of the insert part 1.

An illuminating light supply unit 30 for supplying illuminating light to the light guide fiber bundle 9 is detachably attached to a side of the control mechanism portion 5.

The illuminating light supply unit 30 usually contains a light source lamp that emits illuminating light which is to be supplied to the light guide fiber bundle 9, and a battery serving as a power supply for lighting the light source lamp. In this embodiment, however, the battery is removed from the illuminating light supply unit 30, and a connecting cable 61 which is connected to an AC/DC adapter 60 is connected to the illuminating light supply unit 30.

Figure 2:
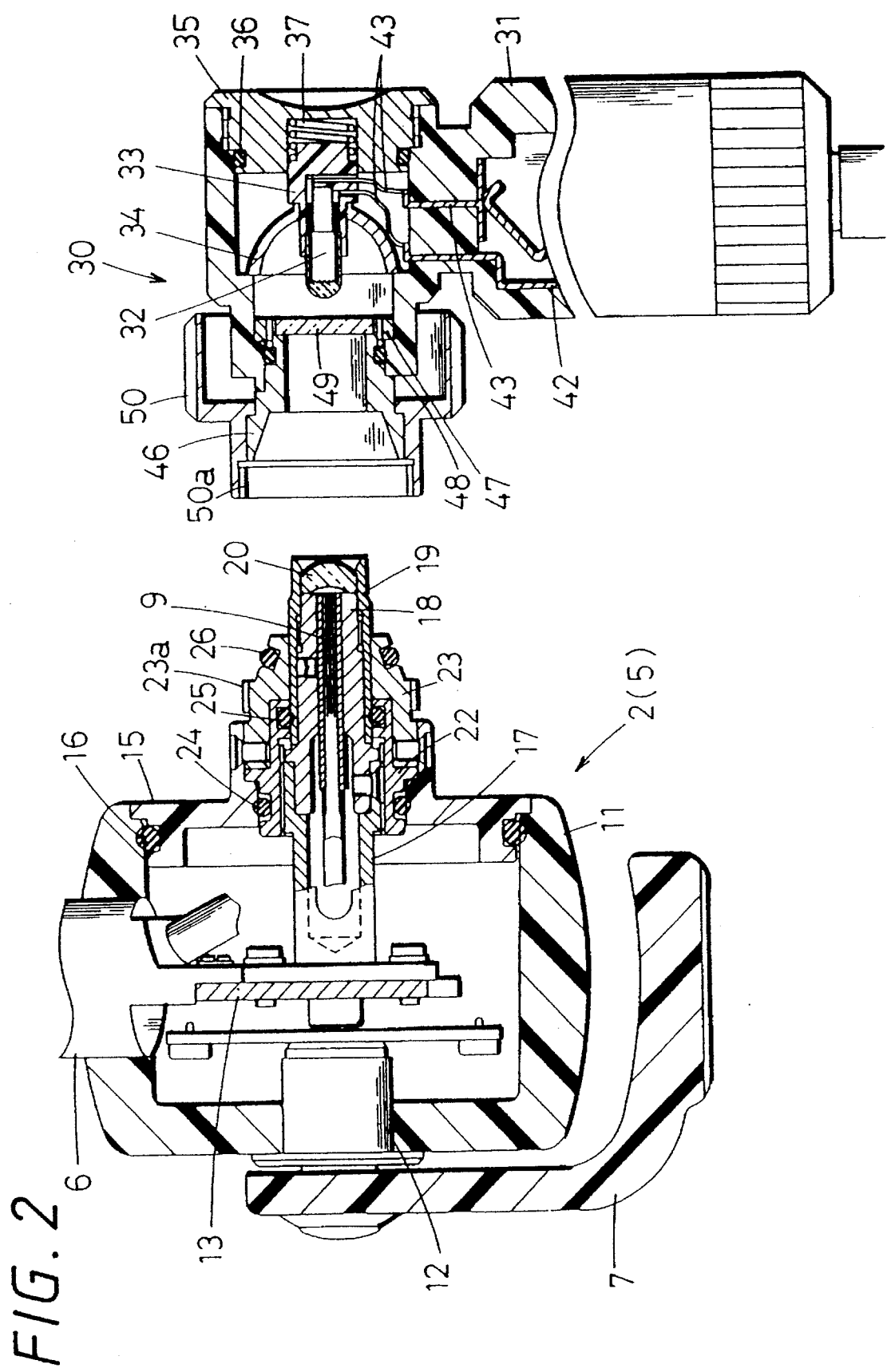
FIG. 2 is an enlarged sectional plan view showing the First embodiment of the present invention with the illuminating light supply unit detached from the endoscope control part.

FIG. 2 is an enlarged sectional view showing the portable endoscope system in a state where the illuminating light supply unit 30 is detached from the control part 2.

The control mechanism portion 5 of the control part 2 is armored with a casing 11 made of a plastic material. A lever bearing cylinder 12 that supports the bending control lever 7 is fitted in a through-hole provided in the casing 11, and sealed in a watertight manner. Similarly, the suction control valve 6 is fitted in a through-hole provided in the casing 11, and sealed in a watertight manner. The respective proximal end portions of the lever bearing cylinder 12 and the suction control valve 6 are secured to a frame 12 in the control part 2.

A cover 15 is flitted in a relatively large opening provided in a side of the casing 11, and a sealing O-ring 16 is attached to the flitting surface of the cover 15 to prevent water from entering the inside of the control part 2 through the gap between the cover 15 and the peripheral wall of the opening. It should be noted that the O-ring 16 is compressed when it is fitted between the cover 15 and the casing 11. However, the cross-section of the O-ring 16 is shown in FIG. 2 in an uncompressed state, i.e.,as a circle is (the same shall apply hereinafter).

A support cylinder 17 is disposed on the central axis of a bore formed in the center of the cover 15. The proximal end portion of the support cylinder 17 is secured to the frame 13 in the control part 2. A light guide mounting cylinder 18 is screwed to the support cylinder 17. The distal end portion of the light guide mounting cylinder 18 projects outwardly from the support cylinder 17. The entrance end portion of the light guide fiber bundle 9 is secured with a screw at the central axis position in the light guide mounting cylinder 18.

A lens mounting cylinder 19 is fitted on the projecting end portion of the light guide mounting cylinder 18 in a cap-like fashion, and firmly thread-engaged with it. The lens mounting cylinder 19 has a convex meniscus lens 20 which is bonded to the distal end portion thereof in a watertight manner. Thus, the convex meniscus lens 20 is set at, a position close to the entrance end surface of the light guide fiber bundle 9 so as to face it.

An O-ring retaining frame 22 is disposed to surround the joint between the support cylinder 17 and the light guide mounting cylinder 18. The O-ring retaining frame 22 is fitted at the outer surface thereof to the wall of the bore provided in the center of the cover 15, and fitted at the inner surface thereof to the outer surface of the lens mounting cylinder 19. O-rings 24 and 25 are attached to the outer and inner surfaces, respectively, of the O-ring retaining frame 22 to prevent water from entering the inside of the control part 2 through the gap between the O-ring retaining frame 22 and the cover 15 or through the gap between the O-ring retaining frame 22 and the lens mounting cylinder 19.

Thus, the control part 2 is formed into a watertight structure which prevents water from externally entering the control part 2 through any portion thereof. The insert part 1 is similarly formed into a watertight structure, as a matter of course. Accordingly, even when the portable endoscope system is dipped in a disinfectant or other liquid with no illuminating light supply unit attached thereto, there is no fear of the disinfectant or other liquid entering the inside of the endoscope.

A connecting cylinder 23 is disposed to surround an area which extends from the lens mounting cylinder 19 to the O-ring retaining frame 22. The proximal end portion of the connecting cylinder 23 is screwed to the inner surface of the bore in the cover 15. The outer peripheral surface of an intermediate portion of the connecting cylinder 23 is provided with an external thread 23a. The outer peripheral surface of the distal end portion of the connecting cylinder 23, which lies forward of the external thread 23a, is a tapered surface which becomes gradually smaller in diameter toward the distal end. A scaling O-ring 26 is attached to the tapered surface at an intermediate position between the external thread 23a and the distal end.

The illuminating light supply unit 30 has an L-shaped cylindrical configuration as a whole. The illuminating light supply unit 30 has a casing 31 made of a plastic material. A light source lamp 32 is disposed in the bend of the L-shaped casing 31. The light source lamp 32 is attached to a lamp socket 33.

The light source lamp 32 is disposed on the axis of the short cylindrical portion of the L-shaped casing 31. A reflecting mirror 34 is attached to the lamp socket 33 so as to surround the light source lamp 32 in order to converge illuminating light from the light source lamp 32 on the axis of the short cylindrical portion of the L-shaped casing 31, The casing 31 is formed with an opening behind the lamp socket 33. A bottom cover 35 is detachably thread-engaged with the mouth of the opening. A sealing O-ring 36 is disposed between the fitting surfaces of the bottom cover 35 and the casing 31 to prevent water from entering the inside of the illuminating light supply unit 30 through the gap between the bottom cover 35 and time casing 31. In addition, a compression coil spring 37 is interposed between the bottom cover 35 and the lamp socket 33 to secure the lamp socket 33 and the reflecting mirror 34 by resilient force from the spring 37.

A connecting cylinder receiving cylinder 46 is secured in an opening provided at the end of the short cylindrical portion of the L-shaped casing 31 by fastening a nut 47 from the inner side of the casing 31. The connecting cylinder receiving cylinder 46 has a tapered opening which is so shaped as to engage with the tapered surface of the connecting cylinder 23, which is provided on the control part 2.

A scaling O-ring 48 is disposed between the fitting surfaces of the connecting cylinder receiving cylinder 46 and the casing 31 to prevent water from entering the inside of the illuminating light supply unit 30 through the gap therebetween. A plane-parallel transparent plate 49 is bonded to the inner end portion off the connecting cylinder receiving cylinder 46 in a watertight manner. Thus, the illuminating light supply unit 30 is formed into a watertight structure which prevents water from externally entering the illuminating light supply unit 30 through any portion thereof, including other portions thereof (described later).

Further, a fastening ring 50 is attached to the outer peripheral portion of the connecting cylinder receiving cylinder 46 so as not to come off axially. The fastening ring 50 has an internal thread 50a for engagement with the external thread 23a of the connecting cylinder 23.

Figure 3:
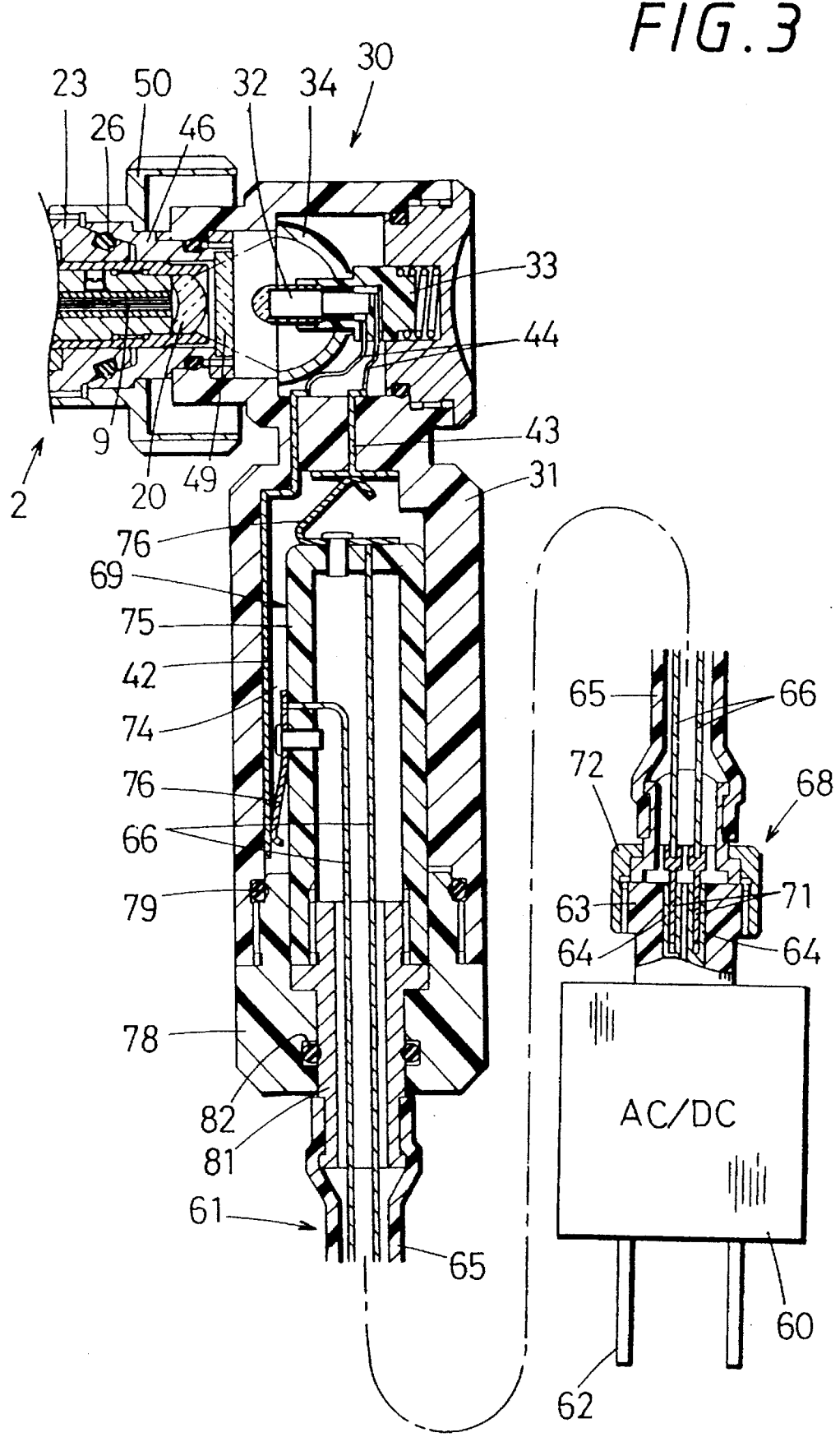
FIG. 3 is an enlarged sectional plan view showing the first embodiment off the present invention with the illuminating light supply unit attached to the endoscope control part.

Accordingly, when the illuminating light supply unit 30 which is in the state shown in FIG. 2 is to be connected to the control part 2, it is brought close to the control part 2, and the tapered surfaces off the connecting cylinder 23 and the connecting cylinder receiving cylinder 46 are brought into close contact with each other. Then, the internal thread 50a of the fastening ring 50 is engaged with the external thread 23a of the connecting cylinder 23. Thus, the illuminating light supply unit 30 is connected to the control part 2, as shown in FIG. 3.

At this time, the O-ring 26, which is attached to the tapered surface of the connecting cylinder 23, is compressed by the connecting cylinder receiving cylinder 46 so as to prevent water from externally entering the joint between the illuminating light supply unit 30 and the control part 2. Accordingly, even when the portable endoscope system is dipped in a disinfectant or other liquid with the illuminating light supply unit 30 attached to the control part 2, there is no fear of the disinfectant or other liquid entering the inside of the endoscope.

In the portable endoscope system having the illuminating light supply unit 30 attached to the control part 2 as described above, illuminating light that is emitted from the light source lamp 32 is reflected by the reflecting mirror 34, and then passes through the transparent plate 49 and the lens 20. Thus, the illuminating light converges on the entrance end surface of the light guide fiber bundle 9, and enters the light guide fiber bundle 9.

Since the connecting cylinder 23 and the connecting cylinder receiving cylinder 46 are brought in close contact with each other at the respective tapered surfaces, the illuminating light supply unit 30 can be immovably secured to the control part 2 by tightly fastening the fastening ring 50 to the connecting cylinder 23.

However, the illuminating light supply unit 30 is allowed to rotate freely about the optical axis of the illuminating light by slightly untightening the fastening ring 50. Accordingly, the illuminating light supply unit 30 can be set in the most convenient position for the user by appropriately adjusting the angle of the illuminating light supply unit 30 relative to the control part 2, which is shown by reference symbol A in FIG. 1, and tightly fastening the fastening ring 50 with the illuminating light supply unit 30 obtained in the desired position.

Figure 4:
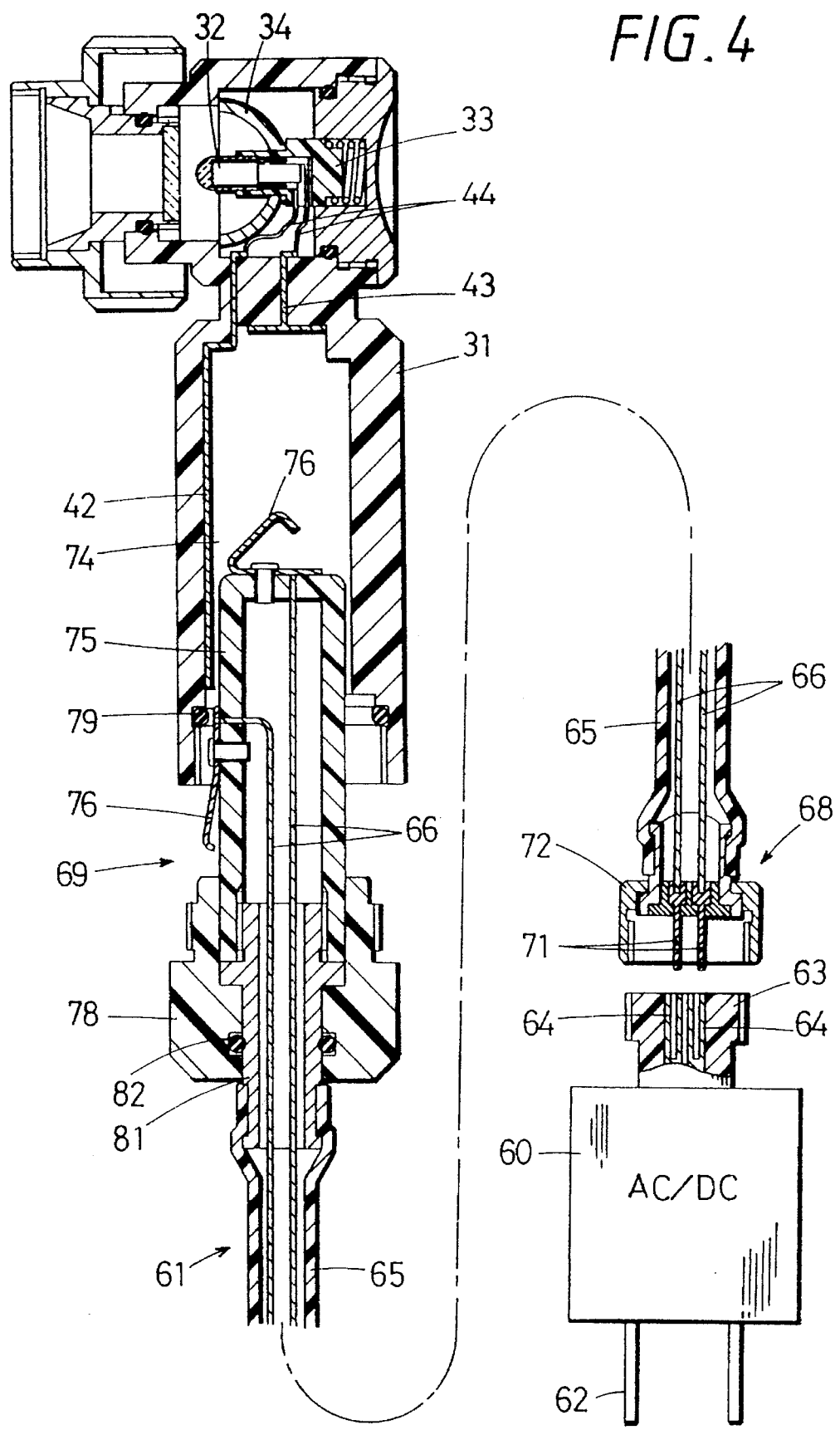
FIG. 4 is an enlarged sectional plan view showing the first embodiment of the present invention in a state where the illuminating light supply unit is disconnected from an AC/DC adapter.

FIG. 3 shows the whole arrangement of the illuminating light supply, unit 30 in a state where it is connected to the control part 2, FIG. 4 shows the illuminating light supply unit 30 in a state where connecting portions at both ends of the connecting cable 61 are disconnected from the illuminating light supply unit 30 and the AC/DC adapter 60, The AC/DC adapter 60 has a plug 62 which can be inserted into an outlet for a commercial AC power supply of 100 V or 200 V, for example, which is supplied for general domestic use. Thus, the commercial AC voltage is converted into a DC voltage which is suitable for lighting the light source Lamp 32, for example, 3 V, and outputted to contacts 64 which are provided in an output terminal portion 63.

The connecting cable 61 is formed from two electric wires 66 which are inserted in a flexible tube 65. The connecting cable 61 has connectors 68 and 69 which are attached to both its ends, respectively.

The connector 68, which is connected to the AC/DC adapter 60, is provided with two contact pins 71 for connecting the electric wires 66 to the contacts 64. The connector 68 is connected to the AC/DC adapter 60 by thread-engaging a fastening ring 72 with the output terminal portion 63, and disconnected therefrom by undoing the thread engagement.

The connector 69, which is connected to the illuminating light supply unit 30, has an electrically insulating plug body 75 which is removably inserted into a battery casing 74 formed in the long cylindrical portion of the L-shaped illuminating light supply unit 30. The plug body 75 has two contacts 76 which are connected to the electric wires 66, respectively. When the plug body 75 is inserted into the battery casing 74, the two contacts 76 come in contact with respective electrodes 42 and 43 which are provided in the casing 31. The electrodes 42 and 43 are connected to the light source lamp 32 through respective lead wires 44.

It should be noted that a switch (not shown) for ON/OFF controlling the light source lamp 32 is provided in an intermediate portion of the wiring for supplying electric power to the light source lamp 32. The switch is also sealed in a watertight manner so that no water can externally enter the inside of the illuminating light supply unit 30.

The plug body 75 has a cover 78 which is provided at the proximal end thereof. The cover 78 is thread-engaged with an opening provided at the distal end of the casing 31. A sealing O-ring 79 is disposed in the boundary between the cover 78 and the casing 31. Further, the plug body 75 is connected to the tube 65 off the connecting cable 61 by a connecting cylinder 81, and a sealing O-ring 82 is disposed between the outer peripheral surface of the connecting cylinder 81 and the inner peripheral surface of the cover 78.

Thus, when the illuminating light supply unit 30 is connected to the AC/DC adapter 60 by the connecting cable 61, the light source lamp 32 is lit up by a DC voltage converted from the AC 100 V supplied from the commercial AC power supply, and illuminating light is supplied to the light guide fiber bundle 9.

It should be noted that, although the AC/DC adapter 60 is not sealed in a watertight manner, the connecting cable 61 is sealed in a watertight manner as a single unit, and the illuminating light supply unit 30 is sealed in a watertight manner by connecting it with the connecting cable 61.

Thus, according to the first embodiment of the present invention, an AC/DC adapter, which is connected to a commercial AC power supply to output a predetermined DC voltage, is connectable to the illuminating light supply unit. Therefore, there is no need off replacing a battery which would otherwise be used in the illuminating light supply unit. Accordingly, an endoscopy can be smoothly conducted without a fear off interruption.

Further, when the connecting cable is connected to the illuminating light supply unit to connect the AC/DC adapter thereto, the illuminating light supply unit is sealed watertight manner so that no water can externally enter the inside of the illuminating light supply unit. Accordingly, the illuminating light supply unit can be washed and disinfected.

Figure 6:
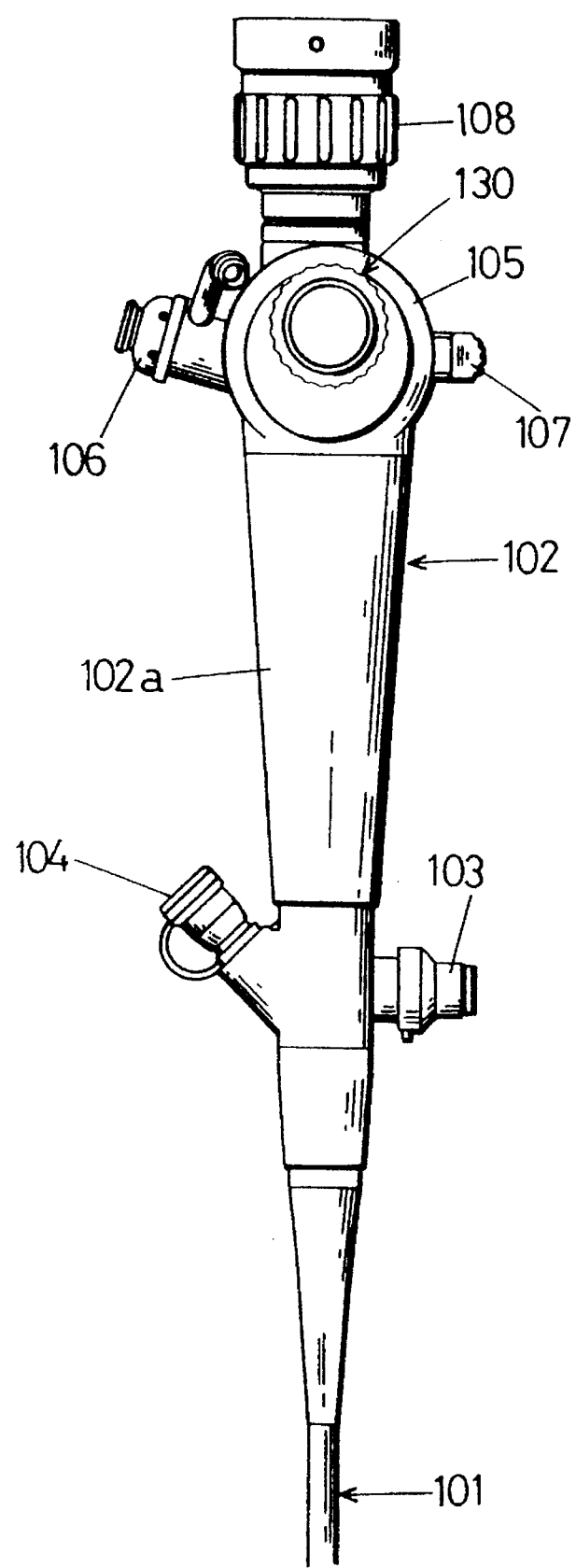
FIG. 6 is a side view of the second embodiment of the portable endoscope system according to the present invention.
Figure 7:
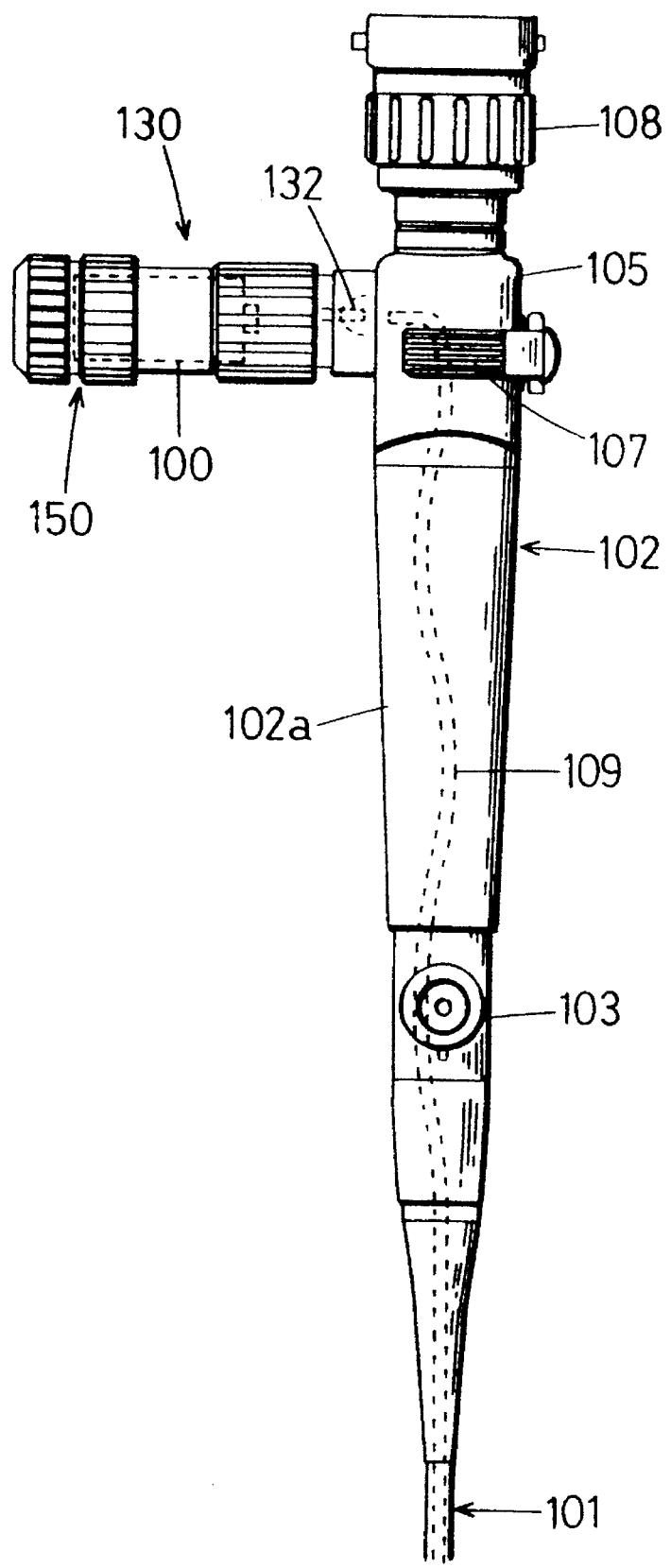
FIG. 7 is a rear view of the second embodiment of the present invention.

FIGS. 6 and 7 are side and rear views, respectively, which show a control part and neighboring constituent elements of a portable endoscope system according to a second embodiment of the present invention. The portable endoscope system has an insert part 101 which is armored with a flexible tube. The proximal end of the insert part 101 is connected to the lower end portion of a control part 102.

About three fourths from the bottom of the control part 102 is a grip portion 102a. A forceps inlet 104 is provided between the grip portion 102a and the insert part 101 so as to project obliquely forward. A pressure control valve 103 is used to control the pressure in the endoscope, which is formed into an airtight structure.

The control part 102 has a control mechanism portion 105 above the grip portion 102a. The control mechanism portion 105 has a suction control valve 106 which is disposed on the front side thereof to carry out a suction operation through a forceps channel. (not shown) inserted in the insert part 101. The control mechanism portion 105 further has a bending control lever 107 which is disposed on the rear side thereof to effect bending control of a remote-controlled bendable portion (not shown) which is formed at the distal end of the insert part 101. In addition, an eyepiece 108 is provided on the top of the control mechanism portion 105.

A light guide fiber bundle 109 for transmitting light For illuminating an object has an entrance end portion thereof disposed in the control mechanism portion 105, and extends through the insert part 101 and the grip portion 102a off the control part 102. The exit end portion of the light guide fiber bundle 109 is disposed in the distal end of the insert part 101.

An illuminating light supply unit 130 for supplying illuminating light to the light guide fiber bundle 109 is detachably attached to a side of the control mechanism portion 105 in such a manner as to project in a straight line perpendicularly to the axis of the control mechanism portion 105.

As shown in FIG. 7, the illuminating light supply unit 130 contains a light source lamp 132 for emitting illuminating light which is to be supplied to the light guide fiber bundle 109, and a battery 100 as a power supply for lighting the light source lamp 132. The battery 100 may be any type of battery, e.g., a dry battery or a rechargeable nickel-cadmium battery.

Figure 8:
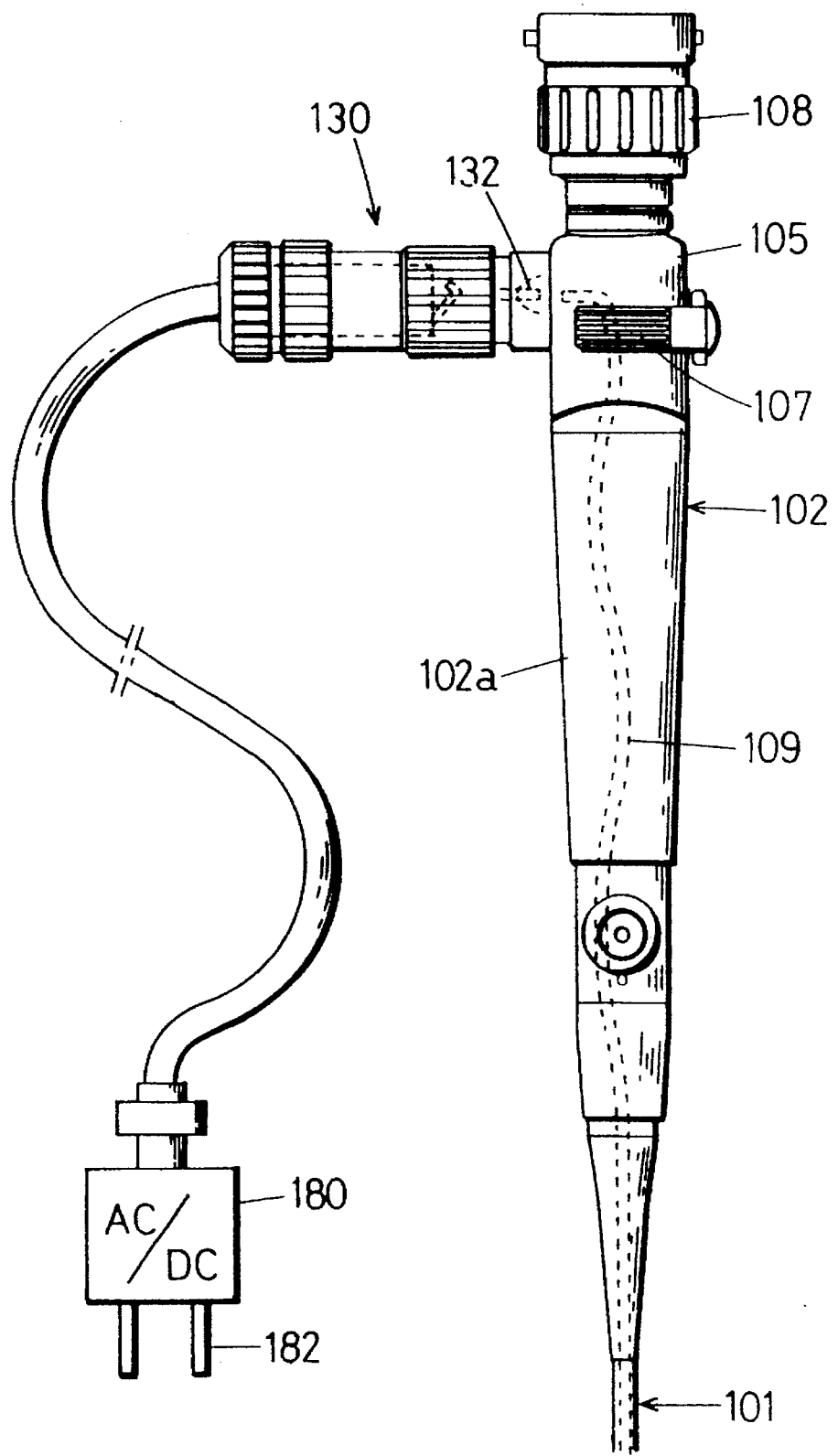
FIG. 8 is a rear view showing the second embodiment of the present invention with an AC/DC adapter connected thereto.

The battery 100 can be replaced by removing a cap 150 which is detachably attached to the outer end of the illuminating light supply unit 130. As shown in FIG. 8, an AC/DC adapter 180 may be connected to the illuminating light supply unit 130 in place of the battery 100.

The AC/DC adapter 180 has a plug 182 which can be inserted into an outlet for a commercial AC power supply of 100 V or 200 V, for example, which is supplied for general domestic use. Thus, the commercial AC voltage can be converted into a DC voltage of 3 V, for example, to light the light source lamp 132.

Figure 9:
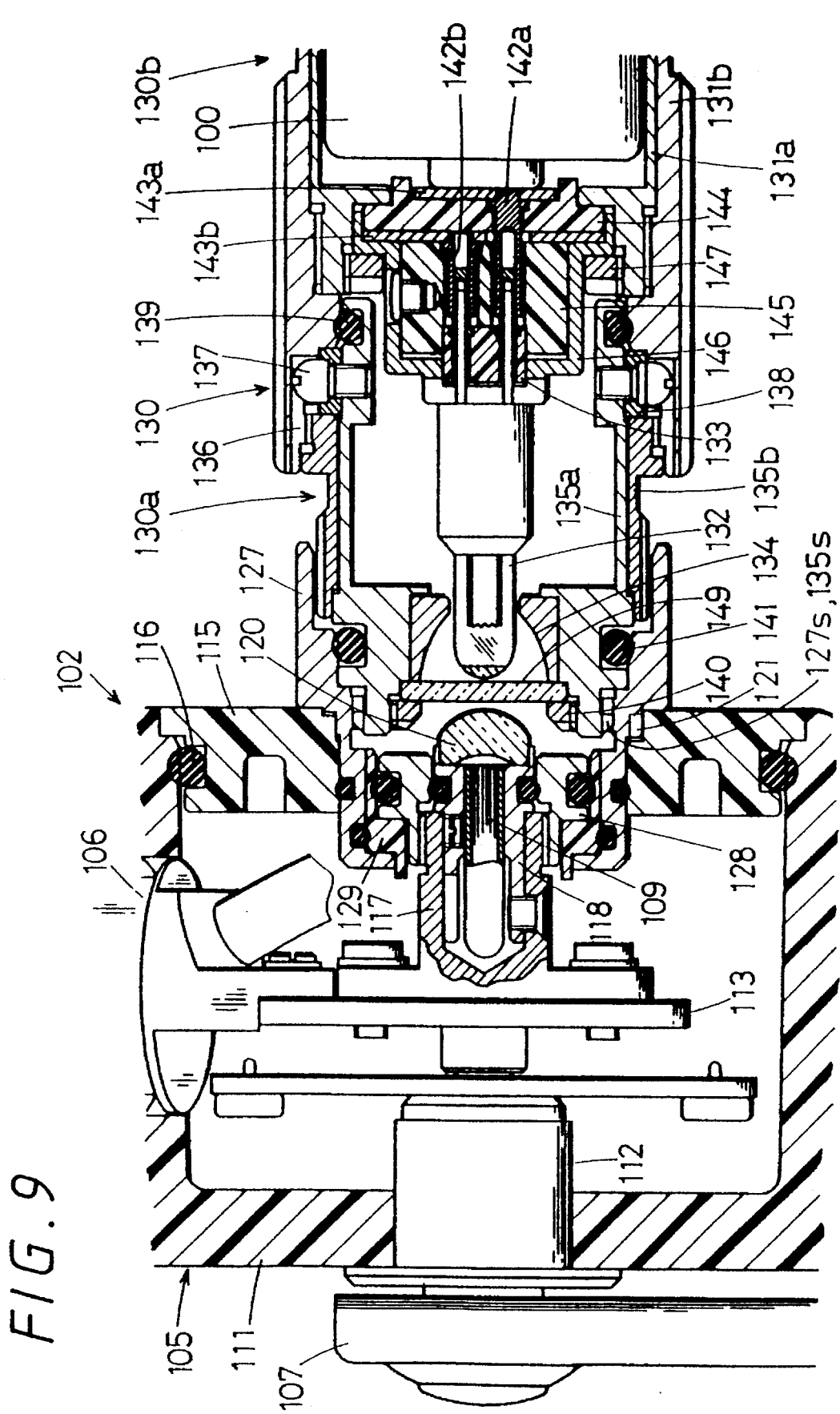
FIG. 9 is a fragmentary sectional view of the second embodiment of the present invention, showing a joint between the endoscope control part and an illuminating light supply unit.

FIG. 9 shows the joint between the control part 102 and the illuminating light supply unit 130 and its vicinities. The control mechanism portion 105 of the control part 102 is armored with a casing 111 made of an electrically insulating plastic material.

A lever bearing cylinder 112 that supports the bending control lever 107 is fitted in a bore provided in the casing 111, and sealed in a watertight manner. Similarly, the suction control valve 106 is fitted in a bore provided in the casing 111, and sealed in a watertight manner. The respective proximal end portions of the lever bearing cylinder 112 and the suction control valve 106 are secured to a frame 113 in the control part 102. The frame 113 is made of a material having mechanical strength and electrical conductivity, such as a metallic material or a carbon resin material (hereinafter referred to as "metal frame 113").

A cover 115 which is made of an electrically insulating plastic material is fitted in a relatively large opening provided in a side of the casing 111, and a sealing O-ring 116 is attached to the fitting surface of the cover 115 to prevent water from entering the inside of the control part 102 through the gap between the cover 115 and the peripheral wall of the opening. In addition, a detent 121 is formed in the area of fit between the cover 115 and the casing 111 to prevent the cover 115 and the casing 111 from rotating relative to each other.

A support cylinder 117 is disposed on the central axis of a through-hole formed in the center of the cover 115. The proximal end portion of the support cylinder 117 is secured to the metal frame 113 in the control part 102. A light guide mounting cylinder 118 is screwed to the support cylinder 117. The distal end portion of the light guide mounting cylinder 118 projects outwardly from the projecting end of the support cylinder 117.

The entrance end portion of the light guide fiber bundle 109 is secured with a screw at the central axis position in the light guide mounting cylinder 118. A convex meniscus lens 120 is bonded to the projecting end portion of the light guide mounting cylinder 118 in a watertight manner so as to face the entrance end surface of the light guide fiber bundle 109.

A cylindrical unit receiving socket 127 is fitted in a through-hole which is formed in the cover 115 such that the socket 127 projects outwardly to receive (connect) the illuminating light supply unit 130, which is detachably attached to the control part 102. The unit receiving socket 127 is made of a stainless steel, for example, and secured by being pressed inwardly with a metallic fastening ring 128 which is thread-engaged with the support cylinder 117.

It should be noted that an insulating cylinder 129, which is made of an electrically insulating plastic material, is interposed between the unit receiving socket 127 and the fastening ring 128 to prevent these members from coming in contact with each other. Thus, the unit receiving socket 127 and the fastening ring 128 are electrically insulated from each other.

Thus, the cover 115 and the insulating cylinder 119, which are in contact with the unit receiving socket 127 provided on the control part 102, are both electrically insulating members. Therefore, even if an external leakage current flows to the unit receiving socket 127, which projects outwardly from the control part 102, the leakage current will not be conducted to the other members of the control part 102.

It should be noted that a sealing O-ring is disposed in the area of fit between each pair of mating members disposed inside the bore of the cover 115, thereby forming the control part 102 into a watertight structure which prevents water frown externally entering the control part 102 through any portion thereof. The insert part 101 is similarly formed into a watertight structure, as a matter of course.

The illuminating light supply unit 130 has a straight cylindrical configuration as a whole. The illuminating light supply unit 130 is divided into a lamp chamber portion 130*a*, which is closer to the joint to the control part 102, and a battery chamber portion 130*b*, which is away from the joint to the control part 102. FIG. 9 shows the whole lamp chamber portion 130*a*.

The outer wall of the battery chamber portion 130*b* is formed from a cylindrical outer casing 131*b* which is made of a material of good corrosion resistance (chemical resistance), for example, a stainless steel, a metallic material which has been subjected to chemical-resistant surface treatment, or a plastic material. Further, a cylindrical inner casing 131*a* is disposed inside the outer casing 131*b* in contact with the inner peripheral surface of the outer casing 131*b*. The inner casing 131*a* is made of a material of good electrical conductivity, for example, copper, or a copper alloy such as phosphor bronze.

A lamp socket 133 is secured to the inner casing 131*a* through some parts at the boundary between the lamp chamber portion 130*a* and the battery chamber portion 130*b*. The light source lamp 132 is detachably inserted into the lamp socket 133. The lamp socket securing structure will be described later.

A cylindrical lamp chamber casing 135*a* constitutes the outer wall of the lamp chamber portion 130*a*. The lamp chamber casing 135*a* is formed of a material of mechanical strength, for example, a stainless steel, and connected to the outer casing 131*b*.

Relative rotation between the lamp chamber casing 135*a* and the outer casing 131*b* is prevented by engagement of a rotation preventing pin 137, which projects from the lamp chamber casing 135*a*, with a groove 136 formed in the outer casing 131*b*.

A securing ring 138 is secured to the lamp chamber casing 135*a* by the rotation preventing pin 137 and held between the outer casing 131*b* and a retaining ring 135*b* which is fitted on the outer periphery of the lamp chamber casing 135*a*, and which is thread-engaged with the outer casing 131*b*. Thus, the lamp chamber casing 135*a* and the outer casing 131*b* are fixed in the axial direction. An O-ring 139 seals the area of joint between the lamp chamber casing 135*a* and the outer casing 131*b*.

A reflecting mirror 134 is bonded to the distal end portion of the lamp chamber casing 135*a* so as to surround the light source lamp 132 in order to converge illuminating light from the light source lamp 132 toward the entrance end surface of the light guide fiber bundle 109.

A transparent cover glass 149 is secured to the front end surface of the reflecting mirror 134 by a retaining nut 140. The outer peripheral surface of the cover glass 149 is coated with a sealing compound to prevent water from externally entering the lamp chamber casing 135*a*.

An O-ring 141 (annular sealing member) is fitted on the outer peripheral surface of the distal end portion of the lamp chamber casing 135*a* so as to come in close contact with the inner peripheral surface of the unit receiving socket 127 in order to seal the joint (i.e., the area between the inner peripheral surface of the unit receiving socket 127 and the outer peripheral surface of the lamp chamber casing 135*a*).

An external thread 135*s* is formed on the outer peripheral surface of the distal end portion of the lamp chamber casing 135*a* at a position which is forward of the O-ring 141. The external thread 135*s* is adapted to engage with an internal thread 127*s* which is formed on the inner peripheral surface of the unit receiving socket 127. Thus, by engaging the two threads 127*s* and 135*s* with each other, the illuminating light supply unit 130 is connected to the control part 102.

Consequently, illuminating light that is emitted from the light source lamp 132 is reflected by the reflecting mirror 134, and then passes through the cover glass 149 and the convex meniscus lens 120. Thus, the illuminating light converges oil the entrance end surface of the light guide fiber bundle 109, and enters the light guide fiber bundle 109.

Thus, in a state where the illuminating light supply unit 130 is connected to the control part 102, the area of fit between the lamp chamber casing 135*a* and the unit receiving socket 127 is sealed by the O-ring 141.

Figure 10:
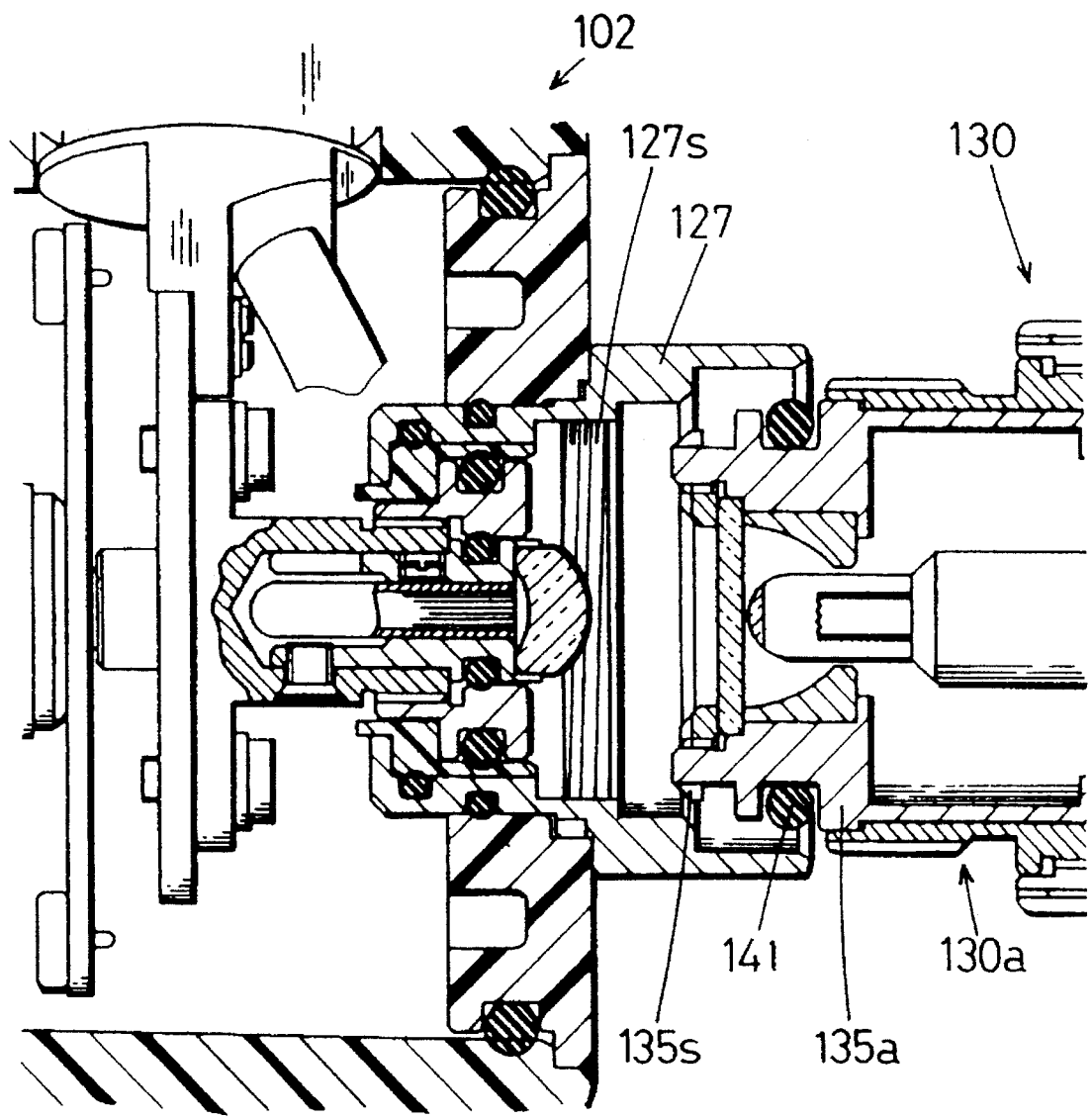
FIG. 10 is a fragmentary sectional view of the second embodiment of the present invention, showing the joint in a state where the illuminating light supply unit is detached from the endoscope control part.

As shown in FIG. 10, by disengaging the external thread 135*s* of the lamp chamber casing 135*a* from the internal thread 127*s* of the unit receiving socket 127, the illuminating light supply unit 130 is detached from the control part 102.

Since in this embodiment the external thread 135*s* is formed on the distal end portion of the lamp chamber casing 135*a* at a position forward of the position at which the O-ring 141 is fitted, the O-ring 141 does not contact the internal thread 127*s* of the unit receiving socket 127 when the illuminating light supply unit 130 is attached to or detached from the control part 102. Accordingly, there is no possibility of the O-ring 141 being damaged when the illuminating light supply unit 130 is attached to or detached from the control part 102.

Referring to FIG. 9, two electrodes which project rearwardly from the light source lamp 132 are inserted into the socket 133 and electrically connected to connecting pins 142*a* and 142*b* which are disposed behind the socket 133. The proximal ends of the connecting pins 142*a* and 142*b* are secured to respective electrode plates 143*a* and 143*b* which are disposed to face each other across an insulating plate 144.

One electrode plate 143*a* is always in contact with the positive electrode of the battery 100, and the other electrode plate 143*b* is electrically connected with the inner casing 131*a* through a retaining cylinder 146 which is made of a metal of good electrical conductivity.

These members are surrounded by an electrically insulating cylinder 145, and secured, together with the socket 133, by being pressed with a retaining nut 147 which is thread-engaged with the inner casing 131*a*.

Figure 11:
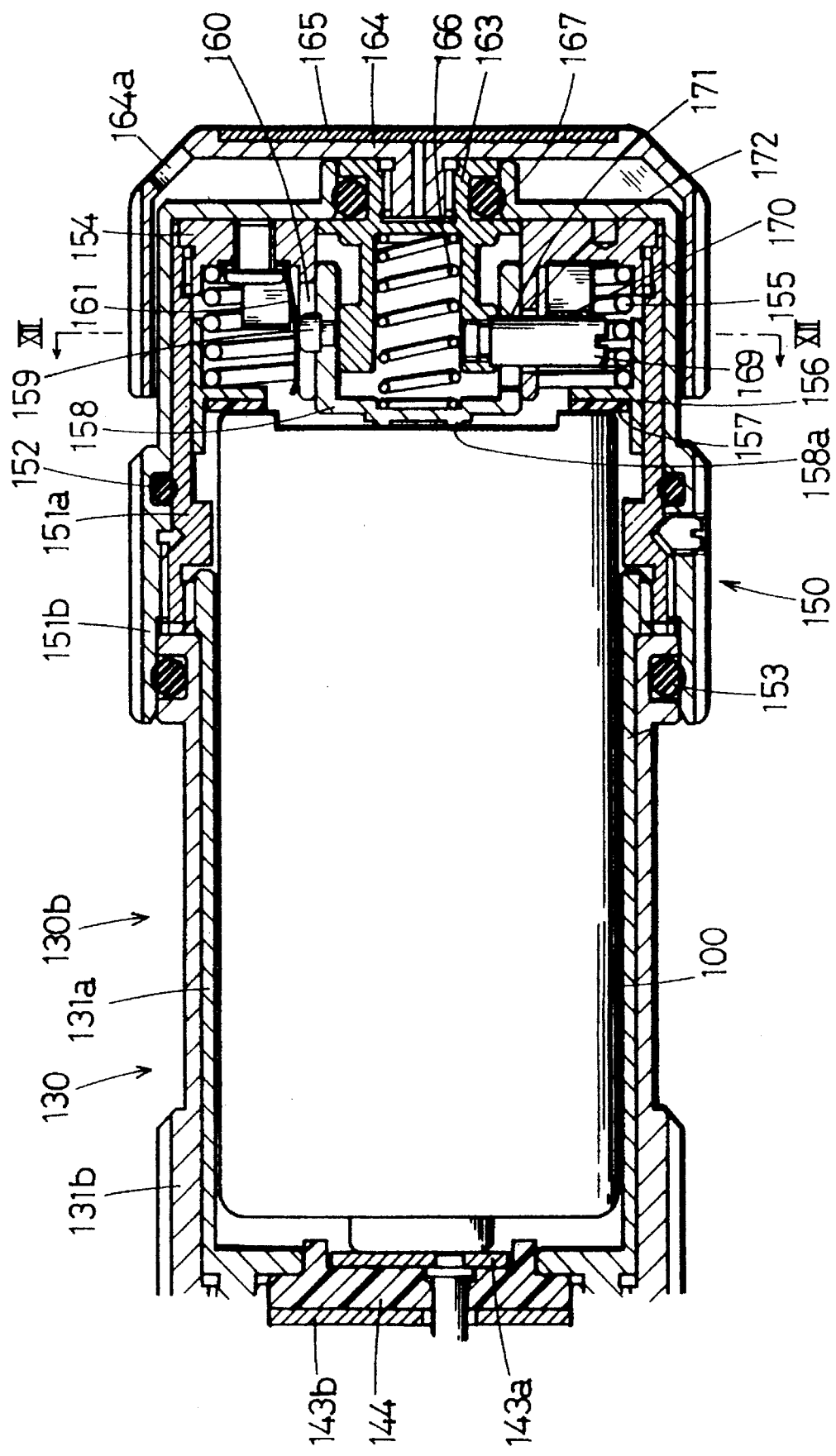
FIG. 11 is a fragmentary sectional view taken along the lines XI—XI, (see FIG. 12), showing a battery chamber and a cap, which constitute a part of the illuminating light supply unit, in the second embodiment of the present invention.

FIG. 11 shows the battery chamber portion 130*b*. A cap 150 is detachably thread-engaged with the end portion of the cylindrical inner casing 131*a*, which accommodates the battery 100. The cap 150 incorporates a switch for ON/OFF controlling the supply of electric power from the battery 100 to the light source lamp 132.

An outer cylinder 151*b* which is made of a material of good corrosion resistance forms the outer wall of the cap 150. An inner cylinder 151*a* which is made of a metal of good electrical conductivity is disposed inside the outer cylinder 151*b* in contact with the inner peripheral surface of the outer cylinder 151*b*. The inner cylinder 151*a* is detachably thread-engaged with the inner casing 131*a*. The outer cylinder 151*b* and the inner cylinder 151*a* are united together by thread engagement and screwing. Reference numeral 152 denotes an O-ring for sealing.

Further, a sealing O-ring (cap sealing O-ring) 153 is disposed in the area of fit between the outer peripheral surface of the battery chamber-side end portion of the outer casing 131*b* and the inner peripheral surface of the outer cylinder 151*b* of the cap 150, thereby preventing water from entering the inside of the cap 150 through the area of fit therebetween.

A cap body 154, which is made of a metal of good electrical conductivity, is integrally connected to the other end portion of the inner cylinder 151a of the cap 150 at the inner side of the outer cylinder 151b by thread engagement and bonding. A first compression coil spring 155 is retained at one end thereof by the cap body 154 to bias the battery 100 toward the lamp chamber portion 130a through a retaining ring 156 which is axially movably fitted in the inner cylinder 151a, thereby ensuring the contact between the positive electrode of the battery 100 and the electrode plate 143a.

It should be noted that the first compression coil spring 155 is disposed in coaxial relation to the battery 100, and the retaining ring 156 abuts on the peripheral edge of the battery 100 so as not to contact the negative electrode of the battery 100. Reference numeral 157 denotes a ring-shaped washer of good slip properties.

A movable contact member 158 contacts the negative electrode of the battery 100. The movable contact member 158 is formed in the shape of a cylinder, one end of which is closed, from a rigid metallic material of good electrical conductivity. The movable contact member 158 is fitted in the cap body 154 so as to be able to axially project from and withdraw into the cap body 154.

The movable contact member 158 has a contact 158a which is formed on the central portion of the bottom of the movable contact member 158. The movable contact member 158 is biased by a second compression coil spring 166 to press the contact 158a against the central portion of the negative electrode of the battery 100.

A guide pin 159 projects from the outer peripheral surface of the movable contact member 158. The guide pin 159 is engaged with an axial guide groove 160 which is formed in the cap body 154, thereby preventing the movable contact member 158 from rotating about the axis. A leaf spring 161 is secured at the proximal end thereof to the cap body 154 to press on the top of the guide pin 159 from the outer side.

Both the guide pin 159 and the leaf spring 161 are formed of a metal of good electrical conductivity. Thus, the negative electrode of the battery 100 is electrically connected to the negative-electrode plate 143b through metallic members of good electrical conductivity which are sealed in the illuminating light supply unit 130 so as to be isolated from the outside, and which are in contact with each other, such as the movable contact member 158, the guide pin 159, the leaf spring 161, the inner cylinder 151a, and the inner casing 131a.

Accordingly, the light source lamp 132 is lit by power supplied from the battery 100 with substantially no drop in voltage in the conducting path. Further, even when the illuminating light supply unit 130 is dipped in a medical fluid, no electrically conducting member will contact the medical fluid. Therefore, no corrosion occurs, and the electrically conducting members are capable of maintaining good electrical conductivity.

A rotating shaft 163 is fitted in the cylindrical movable contact member 158 so as to be rotatable about the axis off the cap 150. A switch control ring 164 is integrally connected by thread engagement and bonding to the head portion of the rotating shaft 163, which projects to the projecting end side off the cap 150.

The switch control ring 164 has a substantially bowl-like configuration, and is disposed so as to surround the end portion of the cap 150. A drainage hole 164a is provided in the outer edge of the switch control ring 164 to discharge water which may enter the space between the switch control ring 164 and the outer cylinder 151b during washing or disinfection.

Although a single drainage hole 164a will suffice in general, a plurality of drainage holes provide good draining performance. Therefore, it is preferable to provide two drainage holes at respective positions which are 180 degrees symmetric with respect to each other. The drainage performance is further improved by providing three or more drainage holes.

Thus, since the drainage hole 164a is provided in the outer edge portion of the switch control ring 164, water entering the space between the switch control ring 164 and the outer cylinder 151b during washing or disinfection can be smoothly discharged, and no water collects in the space at the back of the switch control ring 164. Reference numeral 165 denotes a decorative plate.

The top portion of the movable contact member 158 is rotatably fitted to the inner peripheral surface of the end portion of the outer cylinder 151b. A sealing O-ring (switch sealing O-ring) 167 is disposed in the area of fit between the top portion off the movable contact member 158 and the inner peripheral surface of the outer cylinder 151b, thereby preventing water from entering the inside of the illuminating light supply unit 130. Thus, the illuminating light supply unit 130 is formed into a watertight structure which prevents water from externally entering the inside of the illuminating light supply unit 130 through any portion thereof.

It should be noted that there is no large difference in cross-sectional diameter between the switch sealing O-ring 167 and the cap sealing O-ring 153, but the ring diameter of the cap sealing O-ring 153 is much larger than that of the switch sealing O-ring 167. Accordingly, the sliding resistance to the rotating motion at the area of fit is higher at the cap sealing O-ring 153 than at the switch sealing O-ring 167.

In this embodiment, the ring diameter of the cap sealing O-ring 153 is about 3 times the ring diameter of the switch sealing O-ring 167. However, a noticeable difference can be-produced in the sliding resistance to the rotating motion by providing at least a 2-fold difference in ring diameter.

Figure 12:
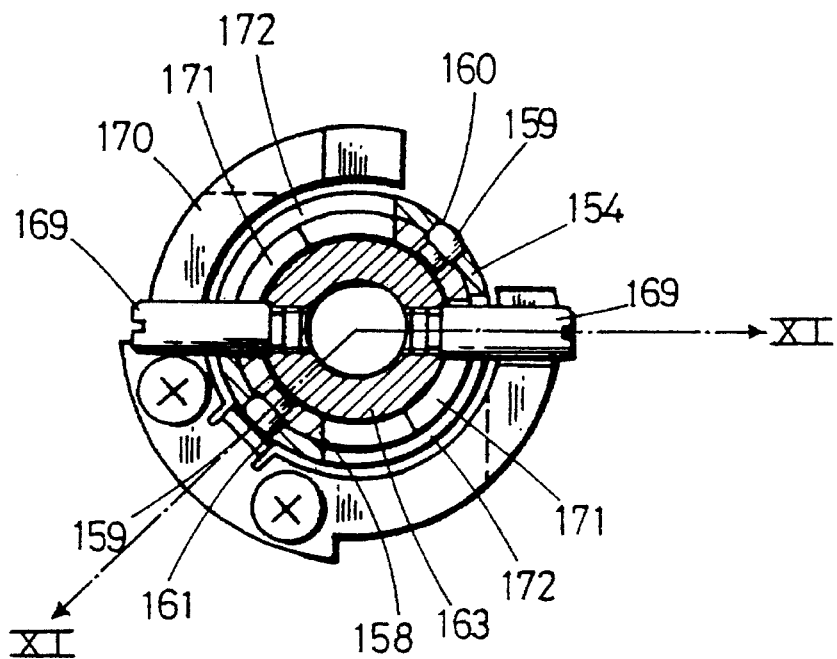
FIG. 12 is a sectional view of the second embodiment taken at a level shown by line XII—XII in FIG. 11.

As shown ill FIG. 12, which is a sectional view taken along the line XII—XII in FIG. 11, lead pins 169 project outwardly from the outer peripheral surface of the rotating shaft 163 at right angles to the axis of the rotating shaft 163. Leaf springs 170 give resistance to the lead pins 169 when these pins 169 reach extremity positions by rotating about the axis of the rotating shaft 163.

The side walls of the movable contact member 158 and the cap body 154, which are pierced with the lead pins 169, are provided with cam grooves 171 and circumferential relief grooves 172. Accordingly, as the lead pins 169 are rotated about the axis of the rotating shaft 163, the movable contact member 158 is forcedly moved axially by the action of the cam grooves 171 against the biasing force of the second compression coil spring 166, causing the contact 158a to separate from the negative electrode of the battery 100. Thus, the light source lamp 132 turns OFF.

Figure 13:
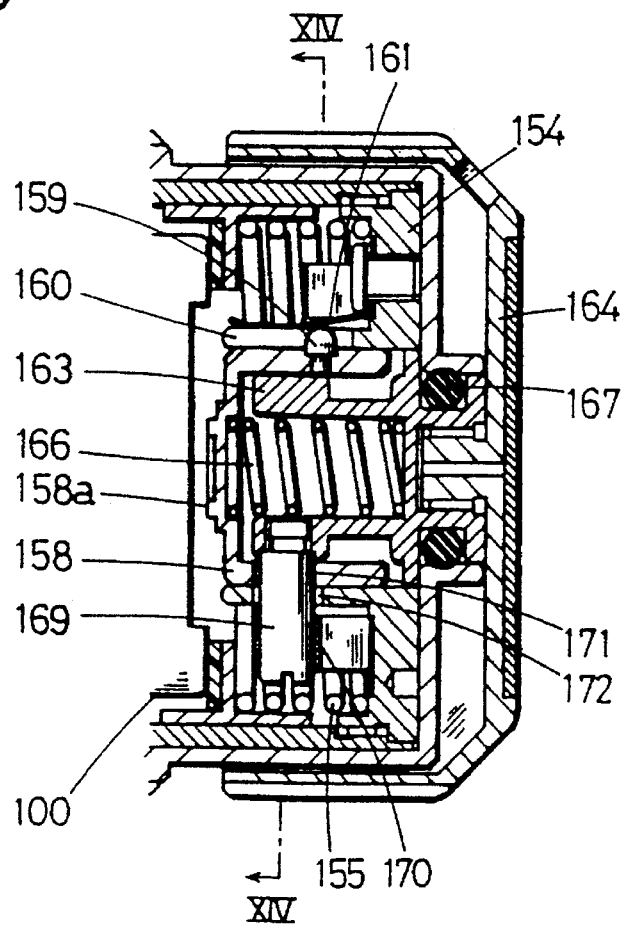
FIG. 13 is a fragmentary sectional view taken along the lines XIII—XIII (see FIG. 14), showing the cap of the illuminating light supply unit in a switch-OFF state in the second embodiment of the present invention.
Figure 14:
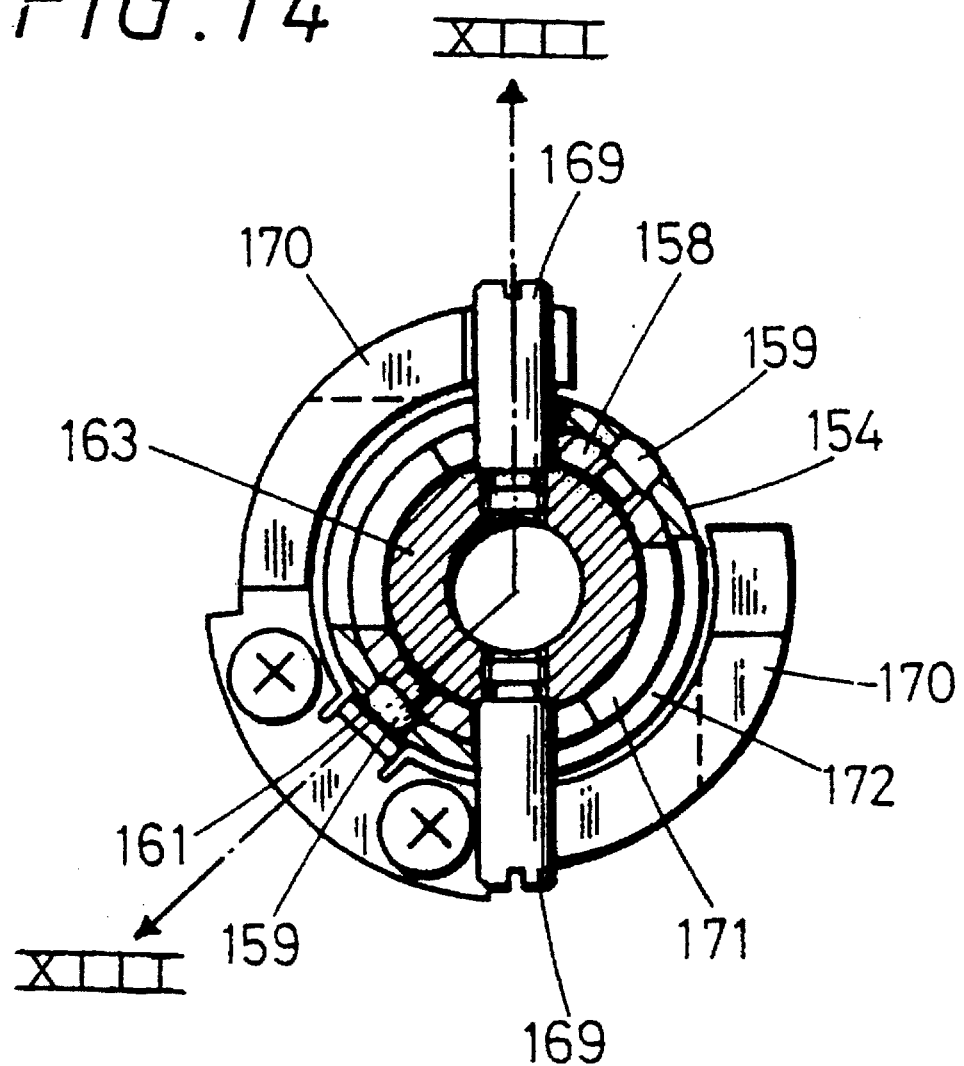
FIG. 14 is a sectional view of the second embodiment taken at a level shown by line XIV—XIV in FIG. 13.

FIG. 13 shows the cap portion of the illuminating light supply unit 130 in a state where the switch is turned OFF by rotating the switch control ring 164 as described above. FIG. 14 is a sectional view taken along the line XIV—XIV in FIG. 13.

In this embodiment, by rotating the switch control ring 164 through 90 degrees from the switch-ON position, the lead pins 169 rotate through the rotating shaft 163, which rotates together with the switch control ring 164 as one unit, causing the movable contact member 158 to move axially by the action of the cam grooves 171. Consequently, the contact 158a is separated from the negative electrode of the battery 100.

The axis of rotation of the switch control ring 164 is coincident with the axis of rotation of the inner cylinder 151a of the cap 150, which is in thread engagement with the inner casing 131a of the battery chamber portion 130b. However, the cap sealing O-ring 153 is greater than the switch sealing O-ring 167 in terms of the ring diameter and hence the sliding resistance, as described above.

Accordingly, when the switch control ring 164 is rotated, the outer cylinder 151b of the cap 150 does not rotate relative to the outer casing 131b of the battery chamber portion 130b, and there is no likelihood that the thread engagement between the inner cylinder 151a of the cap 150 and the inner casing 131a of the battery chamber portion 130b will loosen.

Further, the battery 100 is biased by the first compression coil spring 155 in a direction opposite to the direction in which the movable contact member 158 is separated from the battery 100 by the switching operation. In addition, the first compression coil spring 155, the battery 100, the contact 158a and the second compression coil spring 166 are disposed in coaxial relation to each other. Therefore, the battery 100 is stably held in the battery chamber portion 130b without rattling whether the switch is ON or OFF.

When the cap 150 is to be detached from the illuminating light supply unit 130 to replace the battery 100, it is only necessary for the user to disengage the inner cylinder 151a from the inner casing 131a by rotating the outer cylinder 151b directly with his or her fingers.

It should be noted that, as shown in FIG. 13, the leaf spring 161 for pressing the head portion of the guide pin 159 is bent so that the leaf spring 161 comes out of the state of pressing the guide pin 159 at the very moment the switch-OFF position is reached. Accordingly, a click action takes place at that position, thereby enabling a stable stationary condition to be obtained.

Thus, according to the second embodiment, a unit connecting member for connecting the illuminating light supply unit to the endoscope control part is fixedly connected to the electrically conductive frame of the control part through an electrically insulating member so as to be electrically insulated from the electrically conductive frame. Therefore, even if there is a leakage of electricity from the commercial AC power supply on the illuminating light supply unit side, no current will be conducted to the control pare of the endoscope. Accordingly, it is possible to ensure electrical safety for the patient at all times.

Figure 5:
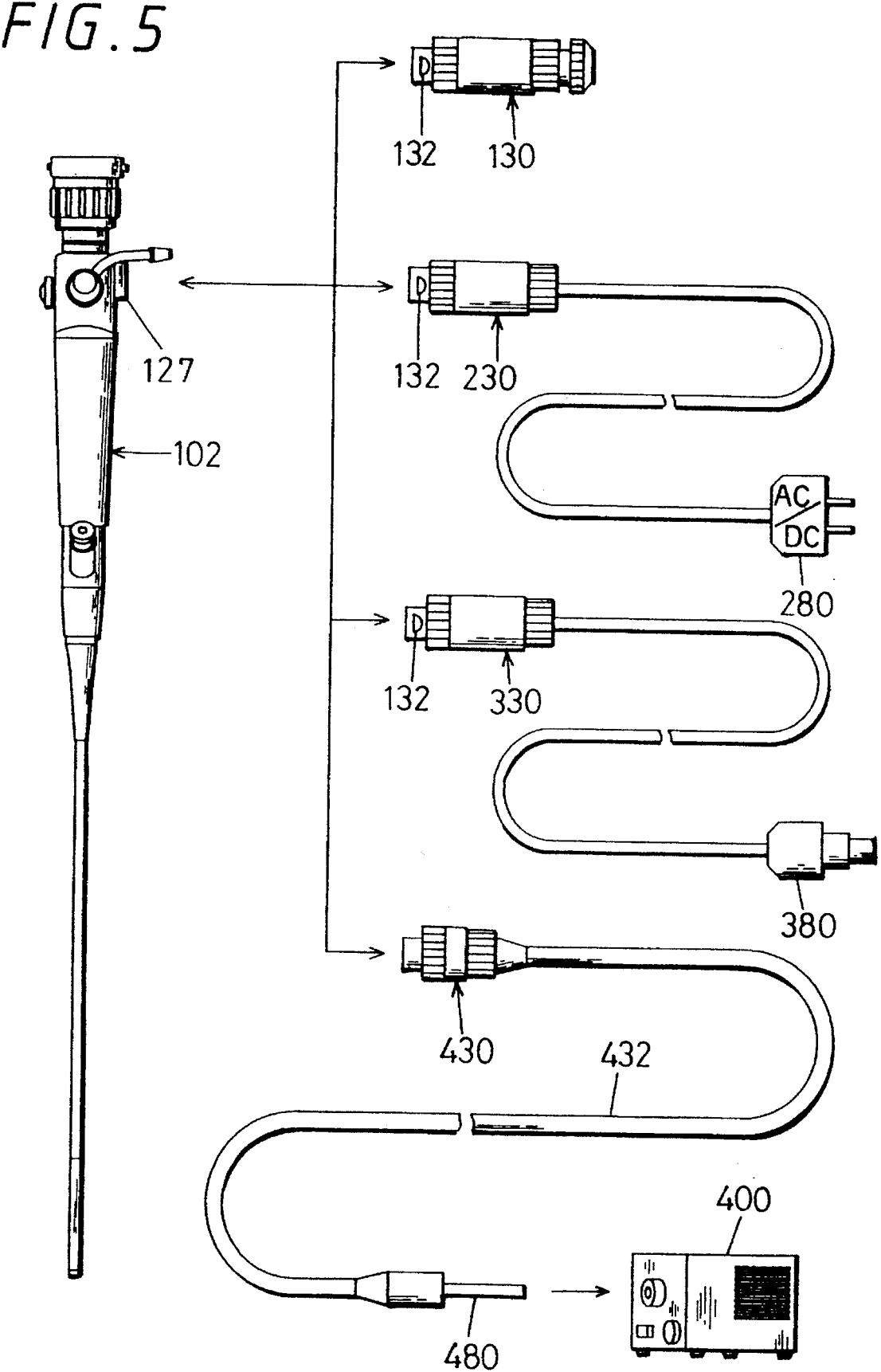
FIG. 5 is a schematic view showing illuminating light supply units which can be selectively connected to a control part of a portable endoscope system according to a second embodiment of the present invention.

FIG. 5 shows illuminating light supply units which can be connected to the control part 102 of the portable endoscope system in the second embodiment. All the illuminating light supply units are adapted to be detachably attached to the unit receiving socket 127. Accordingly, an appropriate illuminating light supply unit can be selectively used according to need.

The first illuminating light supply unit 130, which is shown at the top of the figure, contains a battery for lighting the built-in light source lamp 132. The built-in battery type illuminating light supply unit 130 is the one that has been explained in detail with reference to FIG. 9 and other figures.

The second illuminating light supply unit 230 is an AC/DC conversion type illuminating light supply unit which has an AC/DC converter 280 which is inserted into a commercial AC power supply of 100 V (or 200 V), for example, to convert the AC voltage into a DC voltage suitable for lighting the built-in light source lamp 132, for example, 3 V.

The use of the AC/I)C conversion type illuminating light supply unit 230 enables an endoscopy to be carried out even in a general ward, or the like, without a fear of interruption which might otherwise occur when a battery used for the light source lamp 132 has run down.

The third illuminating light supply unit 330 has a connector 380 which is connected to an external DC power supply (not shown) to light the built-in light source lamp 132 by electric power from the external DC power supply.

If the external DC power supply type illuminating light supply unit 330 is used, an endoscopy can be carried out outdoors, for example, in a disaster-stricken area. If an adapter which is inserted into the socket of an automotive cigar lighter, for example, is used as the connector 380, a storage battery of large capacity can be used as a power supply. It is also easy to charge the power supply. In this case, the DC voltage may be lowered to 3 V, for example, by using a DC/DC converter for transforming a DC voltage, or the like.

The fourth illuminating light supply unit 430, which is shown at the bottom of the figure, is off the light guide cable type in which illuminating light that is emitted from a high-intensity light source lamp (not shown), which is contained in an external light source apparatus 400, is transmitted to the light guide fiber bundle 109 in the endoscope through a light guide cable 432.

The use of the light guide cable type illuminating light supply unit 430 makes it possible to obtain illuminating light of sufficiently high brightness from an external light source lamp, which is considerably bright in comparison to the built-in light source lamp 132, by employing an ordinary light source apparatus for endoscopes.

Thus, in this embodiment, not only a built-in battery type illuminating light supply unit, but also an AC/DC conversion type unit and a light guide cable type unit can be selectively used as an illuminating light supply unit which is detachably attached to the control part. Accordingly, even if the power supply battery for lighting the light source lamp has run down, the endoscopy can be smoothly continued without a fear of interruption. Further, an endoscopy can be carried out even in a general ward or the like.

If the system is arranged so that an external DC power supply type unit can also be use as an illuminating light supply unit, an endoscopy can be carried out outdoors, for example, in a disaster-stricken area, by using an automotive battery or the like.

While the invention has been described by reference to specific embodiments chose for purposes of illustration, it should be apparent that numerous modifications could be made thereto by those skilled in the art without departing from the basic concept and scope of the invention.

We claim:

1. A portable endoscope system having an illuminating light guide for transmitting light for illuminating an object, said illuminating light guide having an entrance end portion disposed in an endoscope control part, and an illuminating light supply unit for supplying illuminating light to said illuminating light guide, said illuminating light supply unit being detachably attached to said control part, said portable endoscope system comprising:

an AC/DC conversion adapter which is connected to an AC power supply to output a predetermined DC voltage, said AC/DC conversion adapter being connectable to said illuminating light supply unit;

wherein said illuminating light supply unit comprises a light source lamp for emitting illuminating light which is supplied to said illuminating light guide, and a battery for supplying lighting energy to said light source lamp, said AC/DC conversion adapter being connected to said illuminating light supply unit through a space defined in said illuminating light supply unit by removal of said battery; and wherein the AC power supply supplies lighting energy to said light source lamp through said AC/DC conversion adapter.

2. A portable endoscope system according to claim 1, wherein said AC/DC conversion adapter is connected to said illuminating light supply unit through a connecting cable, said illuminating light supply unit comprising at least one seal for providing a watertight seal with said connecting cable when said connecting cable is connected to said illuminating supply unit, so that water cannot enter an inside of said illuminating light supply unit.

3. A portable endoscope system according to claim 2, wherein said connecting cable is disconnectable from said AC/DC conversion adapter.

4. A portable endoscope system according to claim 1, wherein said control part has an electrically conductive frame, said illuminating light supply unit being connected to said control part by a unit connecting member which is fixedly connected to said electrically conductive frame through an electrically insulating member so that said unit connecting member is electrically insulated from said electrically conductive frame.

5. A portable endoscope system having an illuminating light guide for transmitting light for illuminating an object, said illuminating light guide having an entrance end portion thereof disposed in an endoscope control part, and an illuminating light supply unit for supplying illuminating light to said illuminating light guide, said illuminating light supply unit being detachably attached to said control part, said portable endoscope system comprising:

illuminating light supply units for selectively being used as said illuminating light supply unit, which is detachably attached to said control part, said illuminating light supply units including, a built-in battery type unit which contains a light source lamp, and a battery for lighting said light source lamp, an AC/DC conversion type unit which has a light source lamp, and an AC/DC converter for obtaining electric power for lighting said light source lamp from a commercial AC power supply, and a light guide cable type unit for transmitting illuminating light from an external light source lamp to said illuminating light guide through a light guide cable.

6. A portable endoscope system according to claim 5, further comprising an external DC power supply type unit for obtaining electric power for lighting a built-in light source lamp from an external DC power supply, said external DC power supply type unit being selectively used as said illuminating light supply unit, which is detachably attached to said control part.

7. A portable endoscope system according to claim 6, wherein said external DC power supply type unit comprises a DC/DC converter for connecting to said external DC power supply and for transforming a DC voltage received therefrom, for supplying electric power to said built-in light source lamp.

8. A portable endoscope system according to claim 5, wherein said control part has an electrically conductive frame, said illuminating light supply unit being connected to said control part by a unit connecting member which is fixedly connected to said electrically conductive frame through an electrically insulating member so that said unit connecting member is electrically insulated from said electrically conductive frame.

9. A portable endoscope system comprising:

an illuminating light guide for transmitting light for illuminating an object, said illuminating light guide having an entrance end portion disposed in an endoscope control part, and an illuminating light supply unit for supplying illuminating light to said illuminating light guide, said illuminating light supply unit being detachably attached to said control part; and a plurality of detachable illuminating light supply units which are selectively attached to said control part to be used as an illuminating light supply unit for the system, said plurality of detachable illuminating light supply units comprising at least two of the units selected from the group consisting of: a built-in battery type unit which contains a light source lamp and a battery for lighting said light source lamp; an AC/DC conversion type unit which has a light source lamp and an AC/DC converter for obtaining electric power for lighting said light source lamp from a commercial AC power supply; a light guide cable unit for transmitting illuminating light from an external light source lamp to said illuminating light guide through a light guide cable; and an external DC power supply unit for obtaining electric power for lighting a built-in light source lamp from an external DC power supply.

* * * * *